(12) United States Patent
Ballew

(10) Patent No.: US 10,751,713 B1
(45) Date of Patent: Aug. 25, 2020

(54) FLUID DISTRIBUTION SYSTEM

(71) Applicant: SANI-TECH WEST, INC., Camarillo, CA (US)

(72) Inventor: Chris Ballew, Thousand Oaks, CA (US)

(73) Assignee: SANI-TECH WEST, INC., Camarillo, CA (US)

( * ) Notice: Subject to any disclaimer, the term of this patent is extended or adjusted under 35 U.S.C. 154(b) by 0 days.

(21) Appl. No.: 16/880,801

(22) Filed: May 21, 2020

(51) Int. Cl.
*B01L 3/00* (2006.01)
*B01D 1/00* (2006.01)
*B01D 24/00* (2006.01)

(52) U.S. Cl.
CPC ............ *B01L 3/502* (2013.01); *B01D 24/005* (2013.01); *B01L 3/5082* (2013.01); *B01D 2313/105* (2013.01)

(58) Field of Classification Search
CPC ...... B01L 3/502; B01L 3/5082; B01D 24/005
See application file for complete search history.

(56) References Cited

U.S. PATENT DOCUMENTS

| | | |
|---|---|---|
| 4,467,846 A | 8/1984 | Croser |
| 4,512,368 A | 4/1985 | Kanunaka et al. |
| 6,032,543 A | 3/2000 | Arthun et al. |
| 6,190,619 B1* | 2/2001 | Kilcoin ............... B01J 19/0046 422/131 |
| 6,779,575 B1 | 8/2004 | Arthun |
| 6,901,948 B2 | 6/2005 | Numberger |
| 2008/0099394 A1 | 5/2008 | Falkner et al. |
| 2011/0067738 A1* | 3/2011 | Molitor .................... B60S 3/04 134/123 |

OTHER PUBLICATIONS

NovaSeptum, Product Specification Sheet, Crimping tool, published Nov. 2003.

\* cited by examiner

*Primary Examiner* — Jennifer Wecker
(74) *Attorney, Agent, or Firm* — SoCal IP Law Group LLP; Guy Cumberbatch; Steven Sereboff

(57) ABSTRACT

There is disclosed a fluid distribution system for distributing fluid from a single source to a plurality of downstream receptacles. The system has a distribution manifold with a single inlet and a plurality of outlets arrayed around a circumferential outer periphery. The outlets may be directed to the different receptacles which each have their own vent filter, or each receptacle connects back to the distribution manifold for common venting.

20 Claims, 8 Drawing Sheets

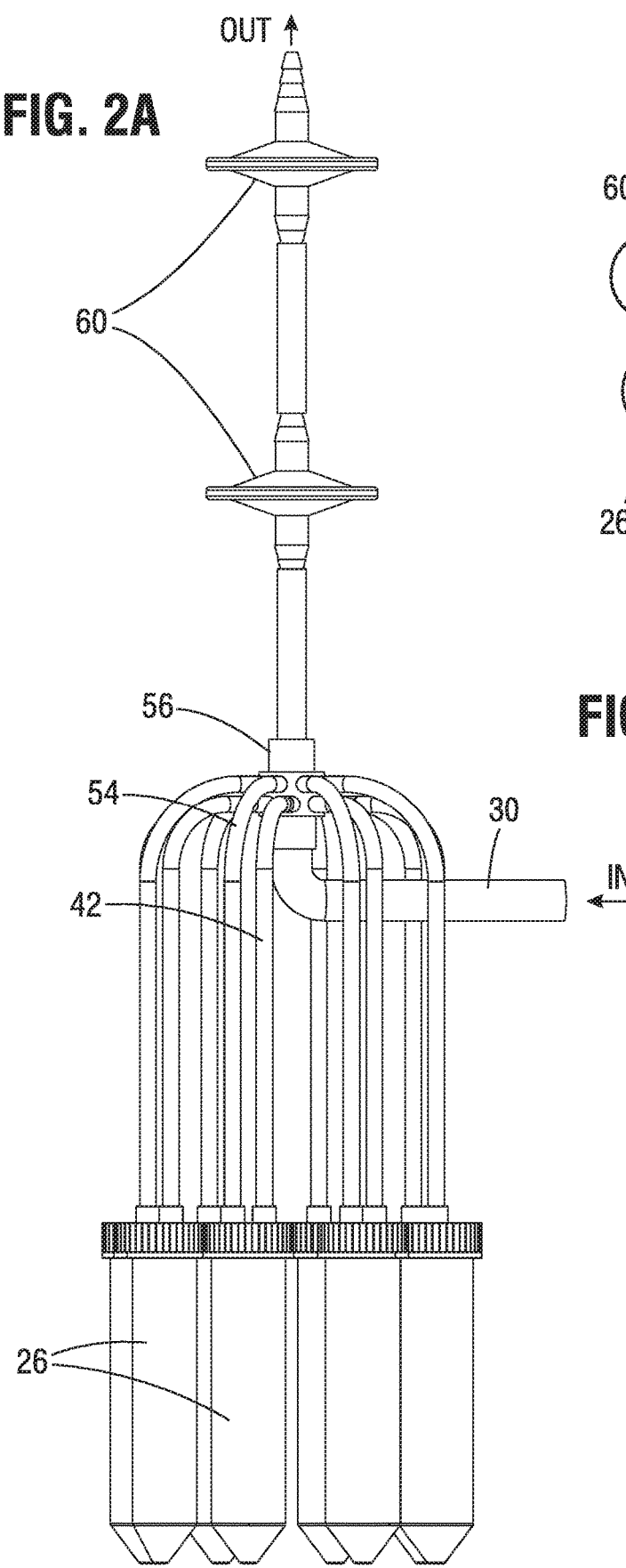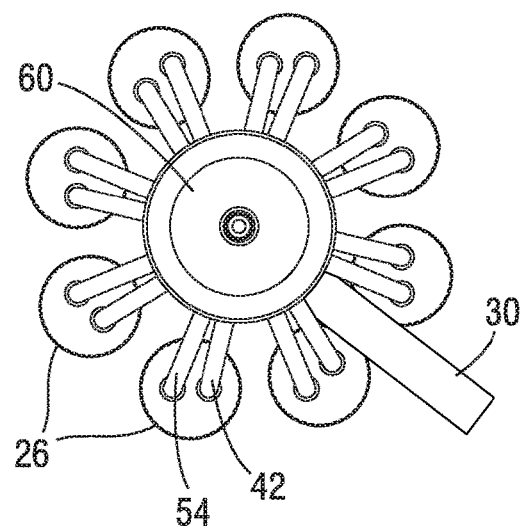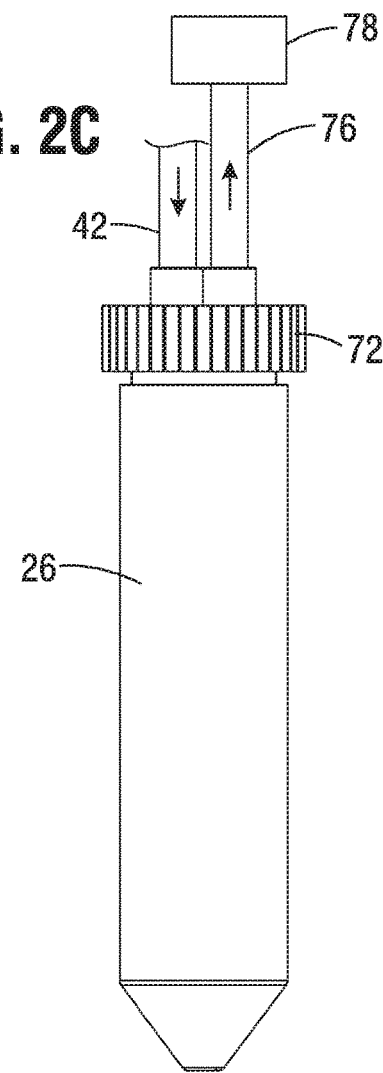

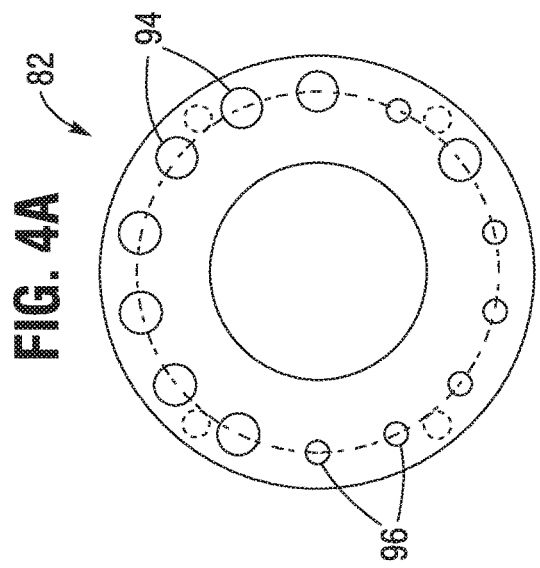
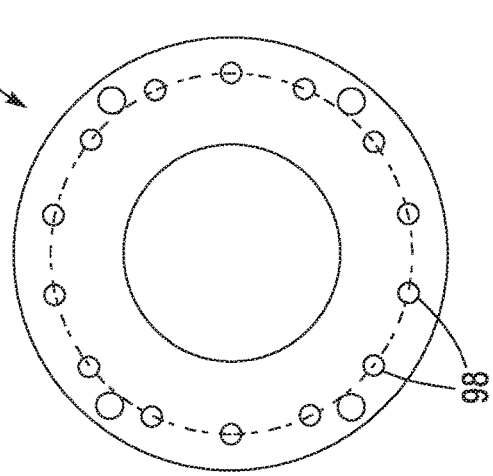
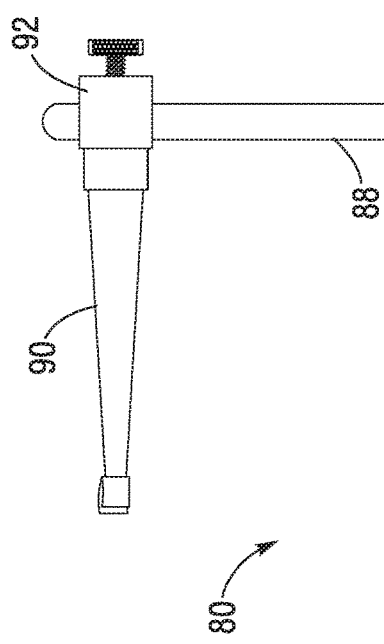
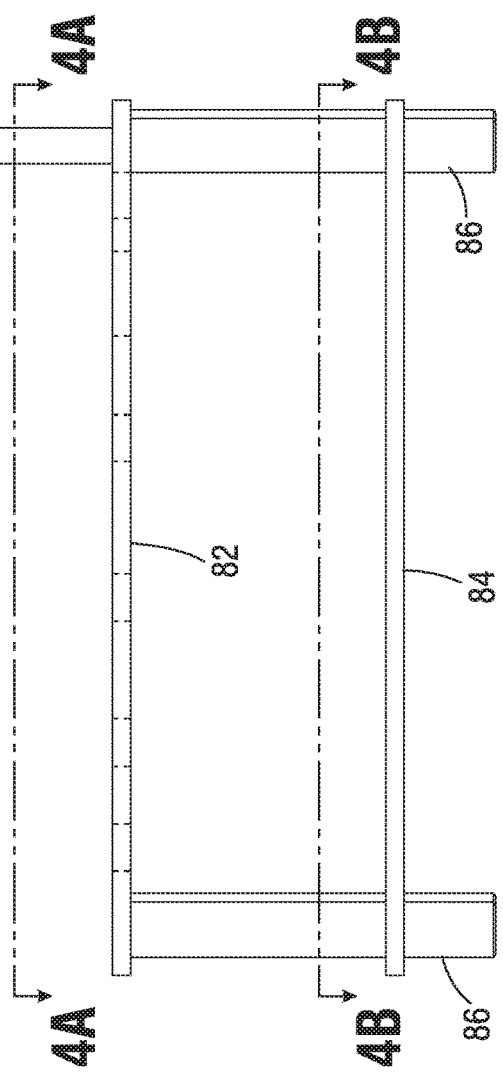

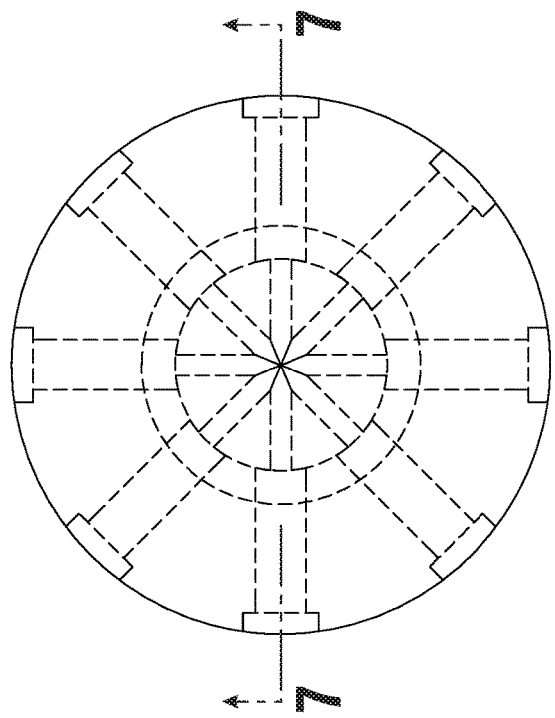
FIG. 6B
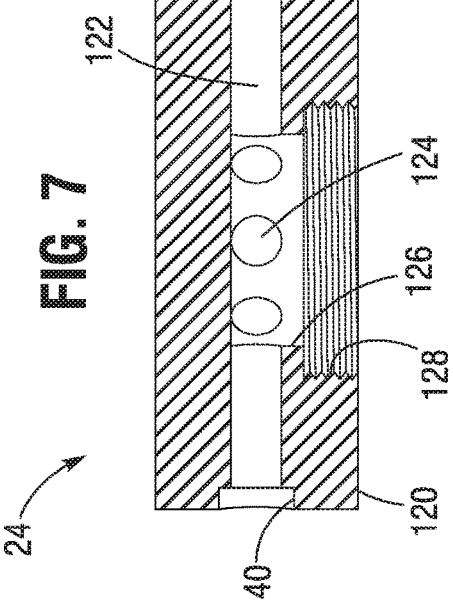
FIG. 7
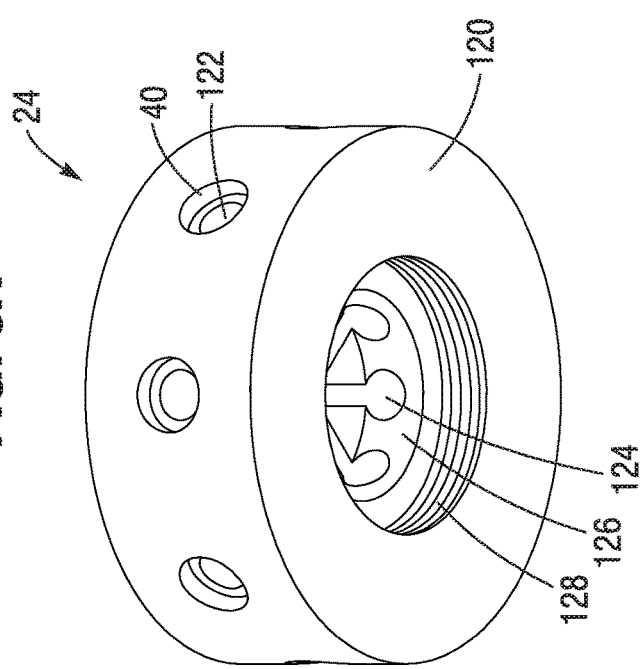
FIG. 6A
FIG. 6C

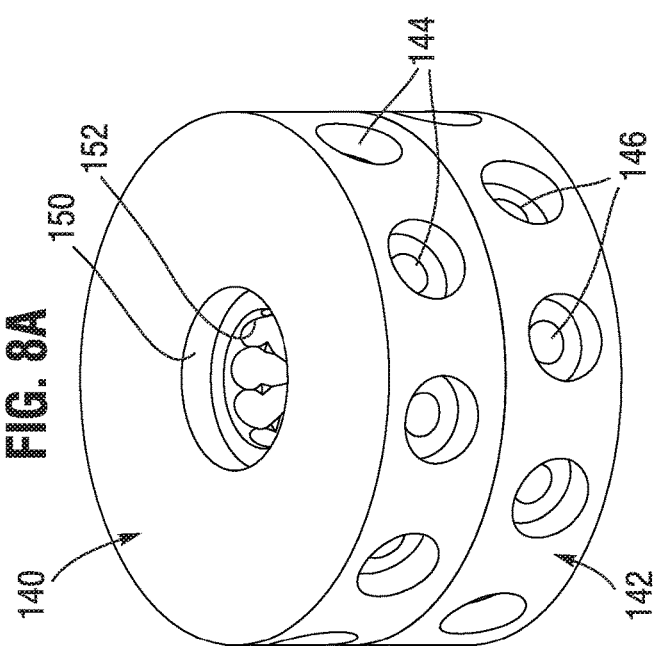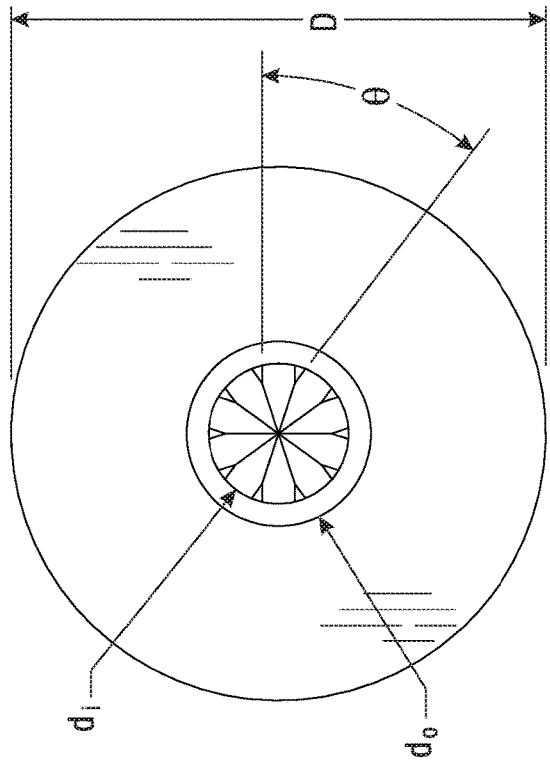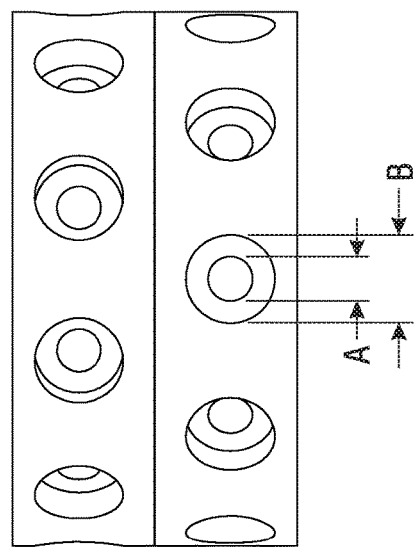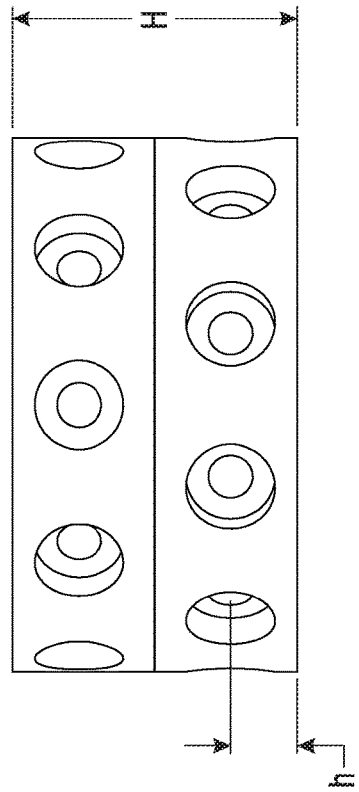

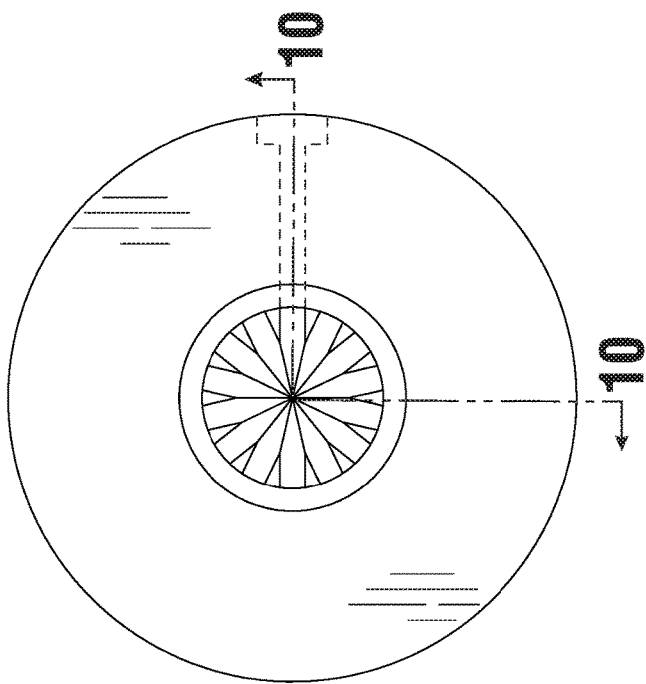
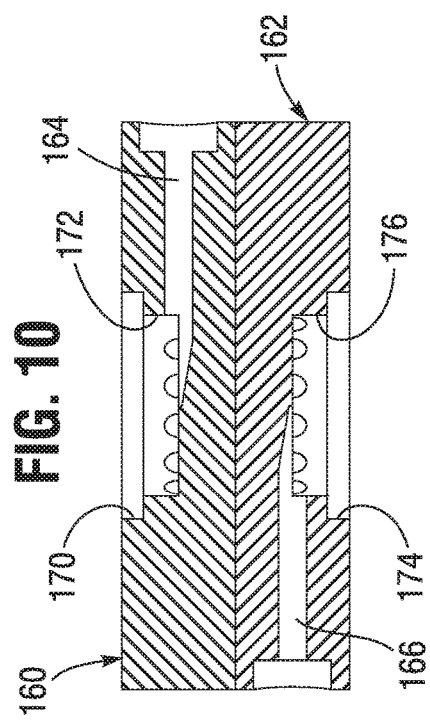
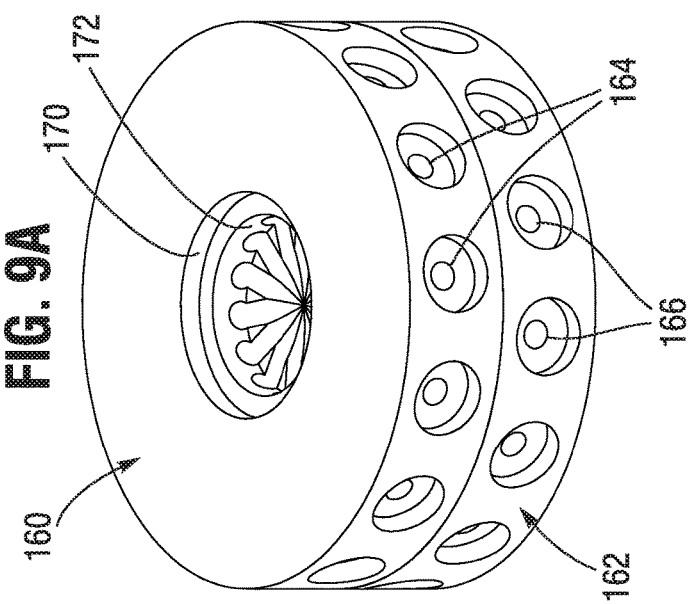
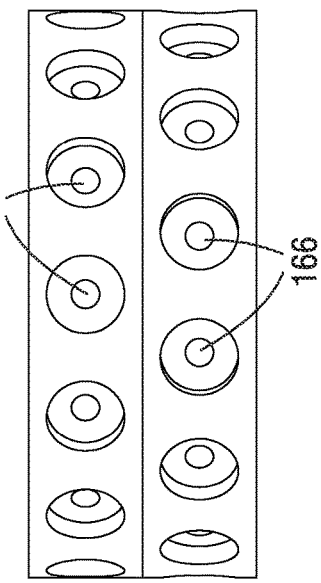

FLUID DISTRIBUTION SYSTEM

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

RELATED APPLICATION INFORMATION

This application is an original filing.

BACKGROUND

Field

This disclosure relates to a biologically closed system for distribution of fluid and, more particularly, to a system for distributing fluid from a single source to a plurality of smaller receptacles.

Description of the Related Art

Processing of fluids in chemical and biological reactors often results in valuable fluid product which must be distributed to smaller receptacles for further processing or delivery to customers. Current systems for distribution of fluids from larger to smaller containers are inefficient.

Current systems make use of linear manifolds leading from a source of fluid to which cross and tee fittings are connected. Fluid enters from one end of the manifold and flows in a linear fashion over each cross or tee branch along the header of the manifold. When liquid flows in this manner, it takes the path of least resistance, and since most of the branches (drops) are smaller in diameter than the manifold header, they receive liquid until hydraulic pressure builds to the point of pressure equalization. This results in uneven filling and requires operator manipulation of valves to assure each container gets filled to the desired level. Manual manipulation like this can cause a mechanical failure of the joints and also create a breach in sterility. The linear design also creates a large footprint and retains large amounts of liquid (hold up volume). This is undesirable because of product value per milliliter or risk to the operator to toxic exposure.

There is a need for a system for rapid distribution of fluid from a single vessel to multiple vessels which provides greater flexibility.

SUMMARY OF THE INVENTION

The present application discloses a fluid distribution system for distributing fluid from a single source to a plurality of downstream receptacles. The system has a distribution manifold with a single inlet and a plurality of outlets arrayed around a circumferential outer periphery. The outlets may be directed to the different receptacles which each have their own vent filter, or each receptacle connects back to the distribution manifold for common venting. The system is especially useful for distributing fluid products from chemical or biological reactors while assuring an integrally closed system.

A multi-channel distribution manifold is disclosed for collecting liquid into containers simultaneously from a single source. If the container is rigid, like a bottle, venting the air that is displaced by the liquid is also needed, and thus a second manifold will be stacked underneath the liquid distribution manifold. All of the vent tubes from the bottles attach to this common hub and share a common vent filter. The distribution manifold can be used just for liquid and each bottle can have its own filter, or the community filter at the central hub may be used. The geometry of the distribution and vent manifolds along with the fusion of the tubes into the housing saves a large amount of space and distributes the fluid evenly in all directions, thus minimizing delays in fluid distribution.

DESCRIPTION OF THE DRAWINGS

FIG. 2A is a side elevational view of the fluid distribution system and FIG. 2B is a top plan view thereof;

FIG. 2C illustrates an alternative configuration of receptacle for use with the fluid distribution system that has a discrete vent filter;

FIG. 4 is a side elevational view of the support stand, and FIGS. 4A and 4B are top plan views of two receptacle support rings thereof;

FIGS. 6A-6C are perspective, plan, and elevational views of a fluid distribution manifold having the capacity for distributing fluid evenly to eight different connected receptacles;

FIG. 7 is a sectional view taken along the line 7-7 in FIG. 6B.

FIGS. 8A-8D are perspective, plan, and elevational views of combined fluid distribution manifold and vent manifolds having the capacity for filling and venting 10 different connected receptacles;

FIGS. 9A-9C are perspective, plan, and elevational views of an alternative combined fluid distribution manifold and vent manifold having the capacity for filling and venting fourteen different connected receptacles; and FIG. 10 is a sectional view taken along the angled line 10-10 in FIG. 9B.

DETAILED DESCRIPTION

Referring now to FIGS. 1-4, an exemplary fluid distribution system 20 is illustrated for distributing fluid from a single source to eight individual receptacles. It should be understood that the illustrated system 20 is just one example, and the concepts disclosed herein can be modified for different systems.

Figure 1:
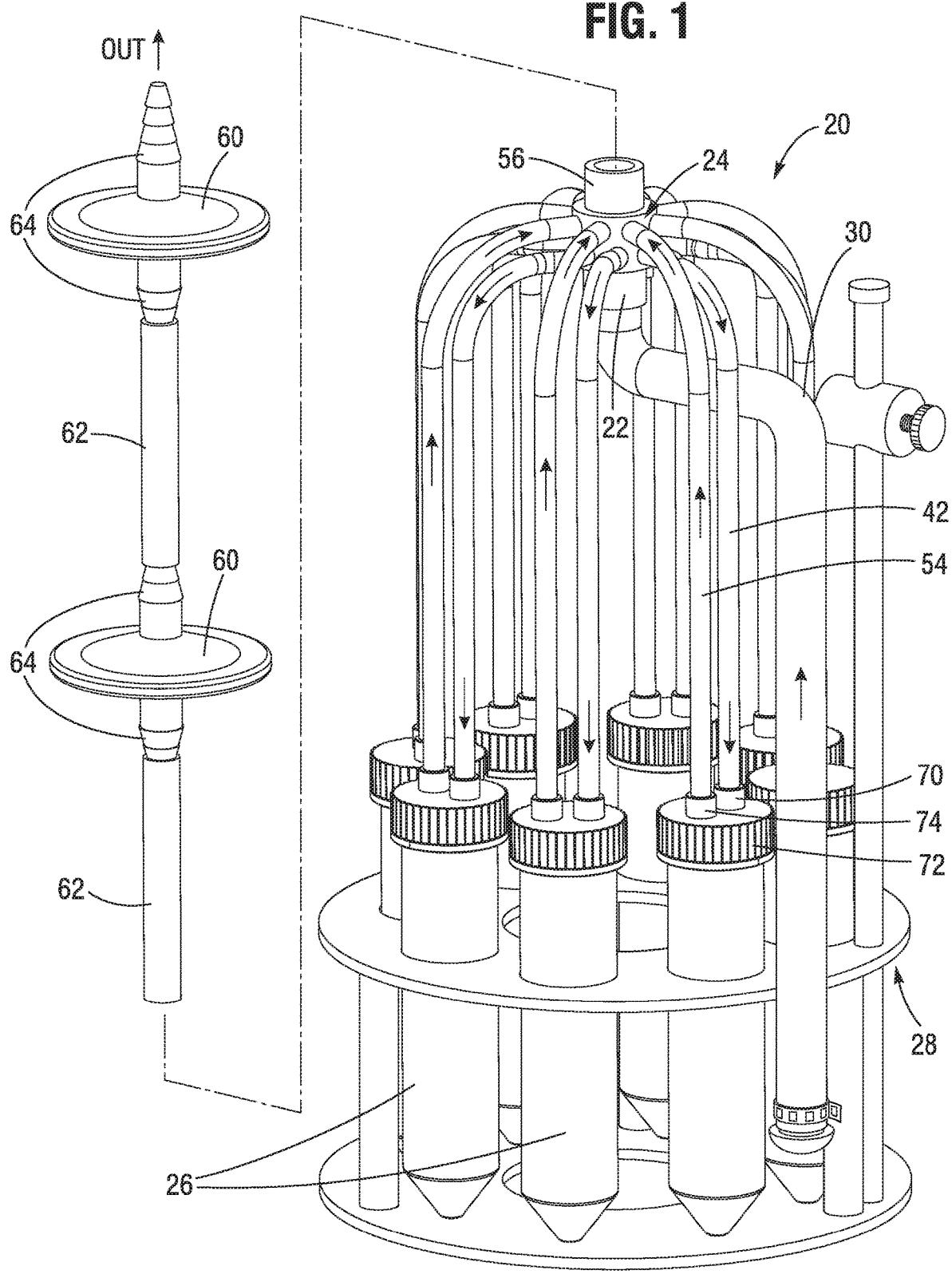
FIG. 1 is a perspective view of an exemplary fluid distribution system for quickly filling eight smaller receptacles from a single source, all supported by a support stand.

In FIGS. 1 and 2A-2B, the exemplary fluid distribution system 20 shows a lower inlet 22 leading to a distribution manifold 24 that separates an inlet fluid flow for delivery to eight individual receptacles 26, all supported by a support stand 28. Although not shown, a source for the inlet flow may comprise a larger vessel, such as a bioreactor vessel or other such chemical processing equipment. The fluid distribution system 20 is especially useful for dividing fluid flow from such a larger vessel into smaller individual receptacles 26, such as the flasks shown. The lower inlet 22 of the distribution manifold 24 located on its underside connects to a larger inlet pipe 30.

Figure 3A:
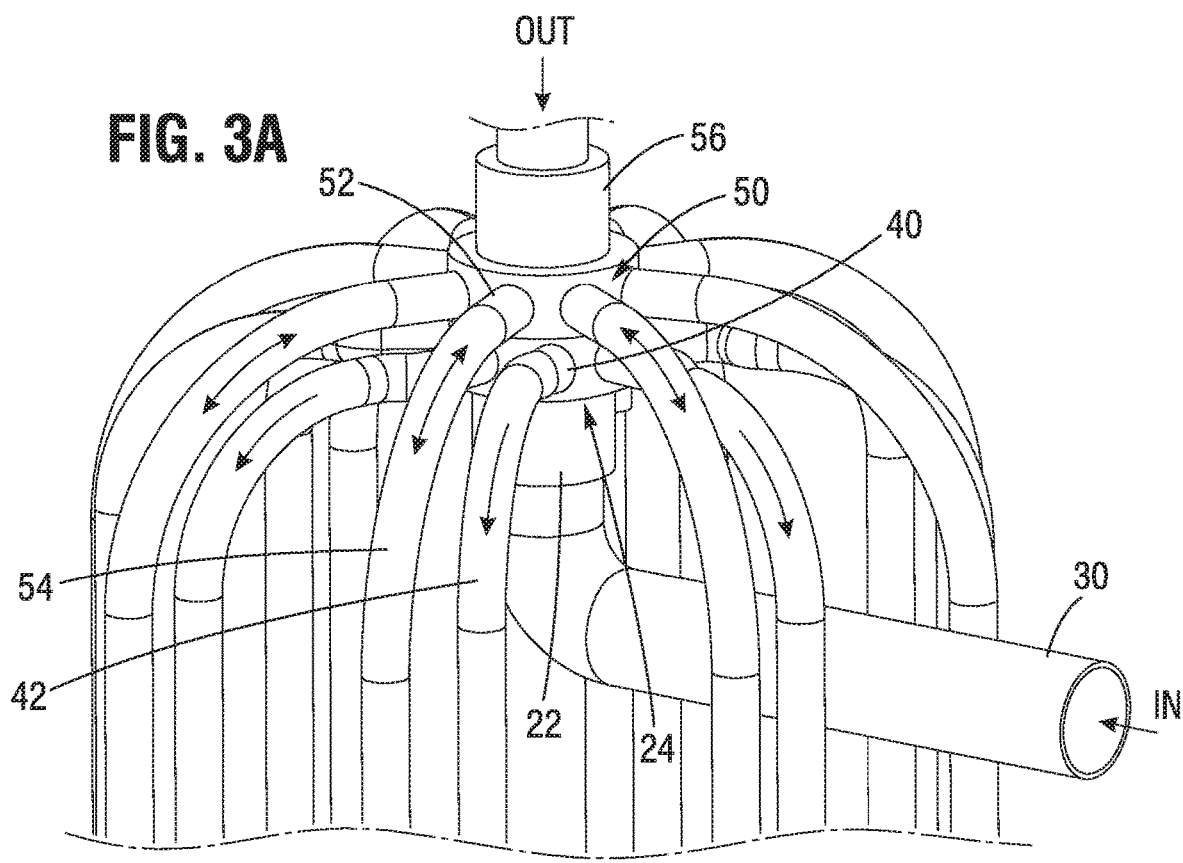
FIGS. 3A and 3B are enlarged perspective and elevational views of a combined fluid distribution and vent manifold for the fluid distribution system with input and output connections shown.
Figure 3B:
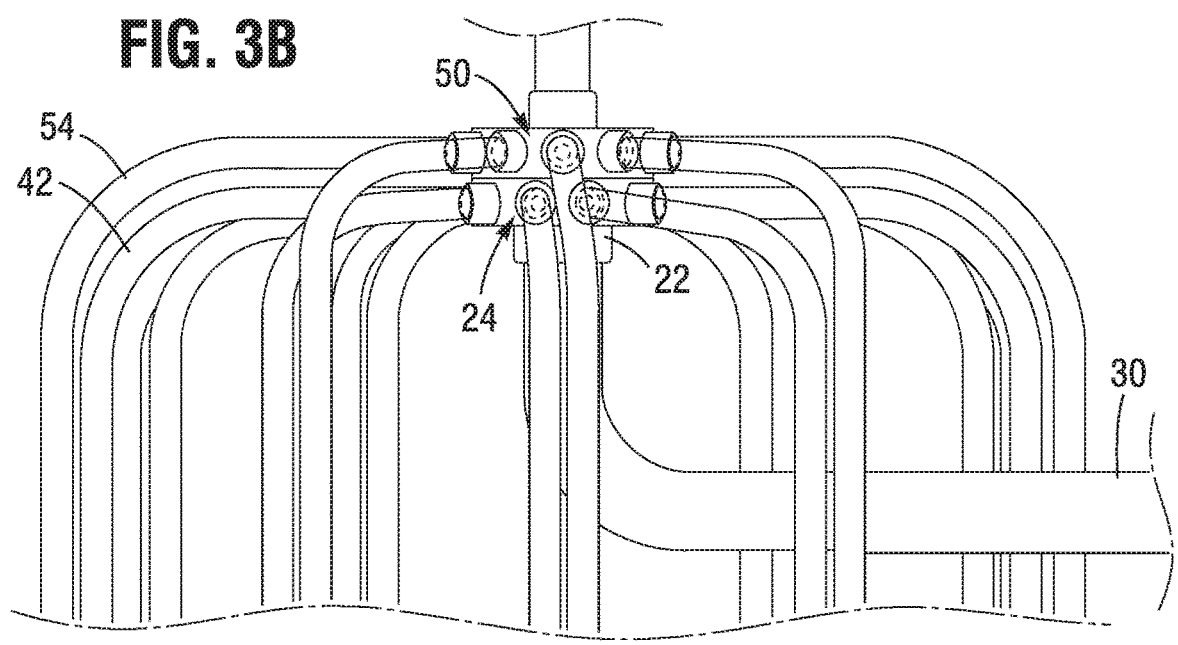

Fluid distribution manifold 24 is seen in the enlarged perspective and elevational views of FIGS. 3A and 3B, and comprises a compact cylindrical body having a plurality of ports or outlets 40 leading to outlet fluid tubes or conduits 42. The conduits 42 may be fused or otherwise bonded into the outlets 40 which are recessed, as described below. As mentioned, there are eight outlets 40 and outlet conduits 42 distributed evenly (45° increments) around the circumference of the cylindrical manifold 24. As will be explained below, internal channels within the manifold 24 direct fluid flowing in through the inlet 22 evenly outward through the outlets 40 and outlet fluid conduits 42.

FIGS. 3A and 3B illustrate a common vent manifold 50 positioned directly above the fluid distribution manifold 24. The vent manifold 50 is similarly shaped with a compact cylindrical body and has a plurality of ports or inlets 52 which receive inlet vent tubes or conduits 54. The conduits 54 may be fused or otherwise bonded into the inlets 52 which are recessed, as described below. The vent manifold 50 has a central outlet 56 located on its upper middle. As will be shown, the vent manifold 50 provides a plurality of internal channels which connect the inlets 52 to the central outlet 56. The central outlet 56 may be directed to be vented into the atmosphere, or may be connected to a common vent filter that filters all of the air displaced from various receptacles 26 during filling.

For instance, as seen in FIG. 1, the gas vented through the central outlet 56 may be filtered through one or more filters 60 connected in line via a plurality of short sections of tubing 62. In the illustrated embodiment, the filters 60 comprise disk-shaped hydrophobic vent filters having inlet and outlet tubing nipples 64 along their central axes. The filters 60 help prevent egress of toxic fluids that may be carried in vaporized form in the vent gasses.

The conduits 40, 54 are desirably tubes made of thermoplastic elastomer (TPE) which be connected in various ways to the manifold ports 40, 52. For instance, the conduits 40, 54 may be attached using hose barb connections with band clamps, tri-clamp flange connections or interference connections with adhesive. For a closed system 20 that is sold ready to be used by a customer, the conduits 40, 54 are molded into the manifold ports 40, 52 and pre-connected in a sealed manner to the receptacles 26. Plugs (not numbered) close the end of the inlet pipe 30 and the end of the last sections of outlet tubing 62. The interior of the system 20 is thus sealed off, aside from the breathable vents 60 which have sufficient filter size to prevent any contamination.

With reference back to FIGS. 1 and 2A-2B, fluid flows in through the inlet pipe 30 to the lower center inlet 22 of the distribution manifold 24. From there, the fluid is evenly distributed outward through the eight outlets 40 and outlet conduits 42. Each of the outlet conduits 42 extends (in this case vertically downward) to a connector 70 in a lid 72 of one of the receptacles 26. As fluid fills each receptacle 26, air or other gas therewithin is displaced upward through a second connector 74 in the lid 72, and upward through the vent conduits 54. The displaced air or gas from each of the conduits 54 is ported inward through the eight inlets 52 (FIG. 3A), and from there to the central outlet 56 and filters 60 along the tubing sections 62. In this way, the combination of the distribution manifold 24 and vent manifold 50 permits filling and venting of the eight receptacles 26 through a single, common location.

FIG. 3A indicates both directions of gas flow for the vent conduits 54. Although not usual, a pressure differential down the conduits 54 may be generated to fill sampling dip tubes (not shown) connected to one or more receptacles 26. Normally the gas flow is upward, though.

It should be understood that each of the receptacles 26 may alternatively have its own separate filter, rather than each receptacle porting vent gas to a common filter location. For instance, FIG. 2C illustrates an alternative configuration where one or more of the receptacles 26 receives fluid through the fluid conduit 42, and vents gas through a short vent conduit 76 leading to a discrete filter 78. Alternatively, the discrete filter 78 may be incorporated into the lid 72 of the receptacle 26. Whichever way the alternative is configured, the receptacle 26 has an individual or discrete gas filter. If all of the receptacles 26 have their own filters 78, the entire vent manifold 50 may be eliminated. The filter 78 is shown in generic form to indicate that it may be a number of different types, including the hydrophobic vent filter 60 described above as well as a simple porous membrane, as the particular process dictates.

Figure 5:
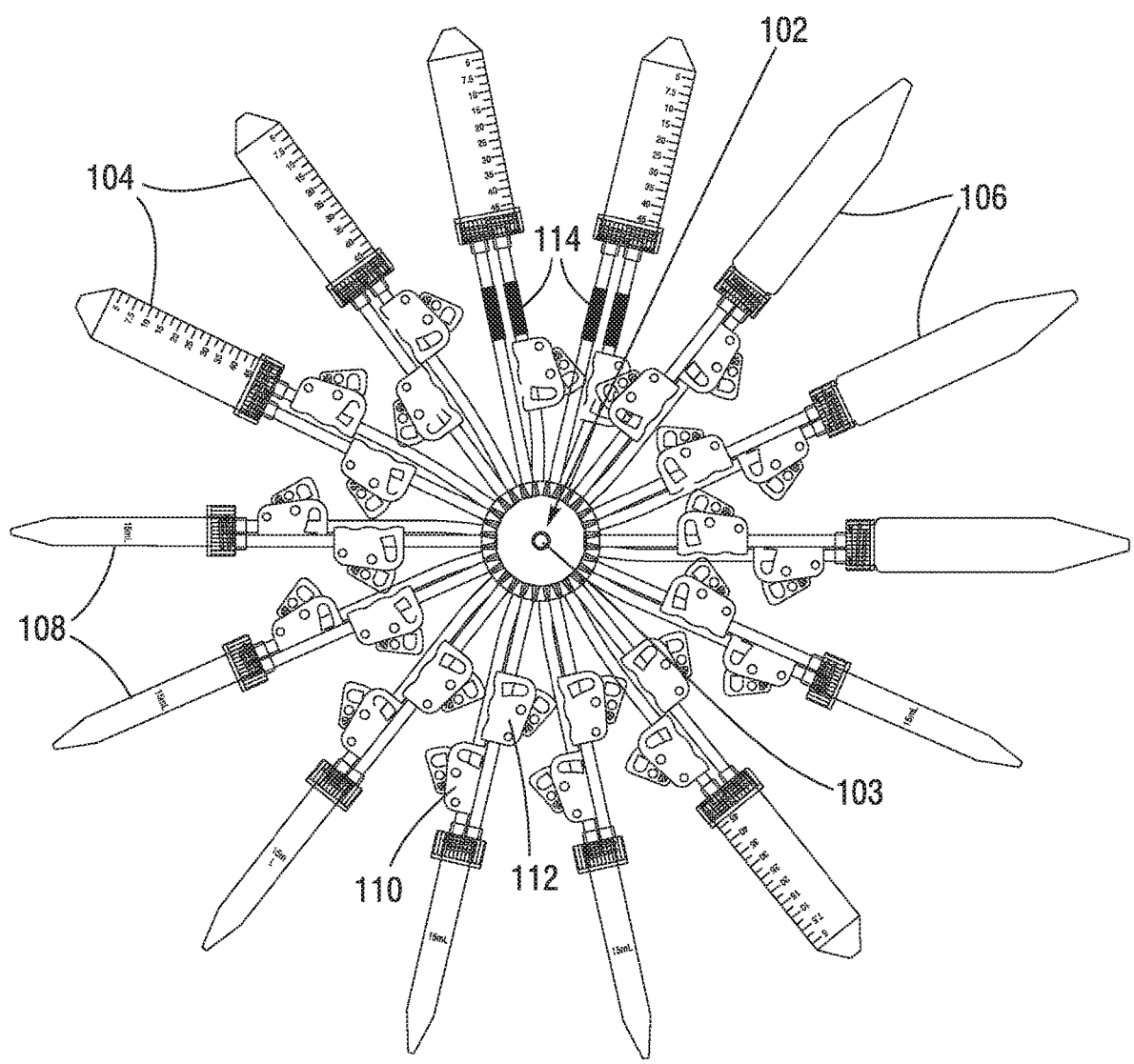
FIG. 5 is a schematic illustration of connections between an exemplary combined fluid distribution and vent manifold and a number of diverse connected receptacles that receive fluid through the manifold from a single source.

FIG. 4 is a side elevational view of a support stand 80 much like the support stand 28 shown above, yet adapted for a diverse set of receptacles, such as one seen in FIG. 5. FIGS. 4A and 4B are top plan views of two receptacle support rings 82, 84 for the support stand 80.

Upper and lower support rings 82, 84 are supported in space parallel relationship by a plurality of vertical legs 86, typically held within aligned through holes (not numbered) in each support ring. An upright post 88 extends upward from the upper support ring 82, and a horizontal arm 90 is secured thereon at variable heights by an adjustable clamp 92. In the embodiment of FIGS. 1-4, the upright post supports the inlet pipe 30, though the horizontal arm 90 can be used to directly support the fluid distribution and vent manifolds.

The upper support ring 82 has a plurality of apertures formed therein that may be arranged around a common concentric circle and are sized to receive a number of the fluid receptacles. In this embodiment, the support ring 82 has large apertures 94 and small apertures 96 sized to closely receive receptacles of different diameters. The lower support ring 84 also includes a plurality of apertures 98 that receive and brace from movement lower ends of the receptacles. For example, FIG. 1 illustrates a number of receptacles 26 having conical bottom ends, wherein the apertures 98 are sized to receive the lower apex of the bottom ends. Similarly, rounded bottom ends on receptacles may be received in the apertures 98. In general, the two support rings 82, 84 provide firm vertical bracing for various forms of receptacles.

FIG. 5 is a schematic illustration of a fluid distribution system 100 showing connections between a combined fluid distribution and vent manifold 102 and a number of diverse connected receptacles. The distribution manifold 102 has an upper vent outlet 103, in this case represented by a through bore of the filter as described above. In this embodiment, the distribution manifold 102 has fourteen outlets (not shown) in fluid communication therewith. As such, there are fourteen outlet conduits (not numbered) extending away from the distribution manifold 102 to fourteen receptacles. A common vent manifold is provided in the distribution manifold 102 and connected to vent conduits (not numbered) returning from the receptacles. Each of the fluid outlet conduits may have a flow control valve 110 positioned thereon for opening and closing flow to that particular receptacle. Likewise, each vent conduit may have a flow control valve 112 positioned thereon to close off that particular receptacle from any back venting from the vent manifold that may be openly connected to the other receptacles. The flow control valves 110, 112 may be simple clamps such as used in medical tubing.

Both the fluid conduits and vent conduits for two of the larger receptacles 104 may have sleeve-like crimping tubes 114 thereon. The crimping tubes 114 enable the conduits to be crimped and thus closed off after filling the respective receptacle. The crimping tubes 114 may be formed of brass, and may be configured to be separated after crimping so as to easily detach the filled receptacle from the overall system. For example, a crimping and separating device such as described in U.S. Pat. No. 6,779,575 to Arthun may be utilized. Further, the conduits may be formed of heat sealable TPE which can be sealed with heat and simply cut off to preserve a filled receptacle for later use.

There are five large receptacles 104 having volumetric indicators thereon. Additionally, there are three medium-size receptacles 106, and six smaller receptacles 108. This combination of receptacles is just one of many that can be connected to the manifold 102, and any number of variations are contemplated. The flow into the receptacles 104, 106, 108 from the common distribution manifold 102 and venting of gas out of the receptacles to a common vent manifold and filter has been described previously and thus will not be repeated. One or more of the fluid conduits may be closed off or plugged if less than the total number will be filled at any one time.

FIGS. 6A-6C are perspective, plan, and elevational views of an exemplary cylindrical fluid distribution manifold 24 having the capacity for evenly filling eight different connected receptacles, such as was described above. This particular distribution manifold 24 may be identical to the vent manifold 50 in the system shown in FIGS. 1-4, and as such the following description applies to both.

The distribution manifold 24 has a solid body 120 that may be molded out of a suitable polymer such as polypropylene. The body 120 has a squat cylindrical configuration with a plurality of the outlets or ports 40 formed therein and distributed evenly around its circumferential outer wall. Preferably, the ports 40 are formed by a recessed step leading to a radial through bore 122. As mentioned, the conduits 42 are easily fused or bonded into the recessed ports 40 for a particular system 20.

Inner apertures 124 of some of the through bores 122 are shown in FIGS. 6A and 7, opening through an inner cylindrical wall 126. The inner cylindrical wall 126 defines a common inner chamber within the distribution manifold 24. The inner wall 126 has an axial height large enough for the inner apertures 124, and then steps radially outward to a second inner cylindrical wall 128 that intersects the lower surface of the body 120. A flat upper surface of the body is closed so that the larger inner wall 128 forms a common opening in communication with each of the outlets 40. The larger inner wall 128 provides a cylindrical recess which either forms the central inlet 22 or provides a convenient recess in which to bond a coupler which connects to the larger inlet pipe 30, as described above. The inlet pipe 30 or inlet coupling 22 is preferably fixed by thermal fusion, thermal welding or bonding within the inner wall 128, or the inner wall 128 may be threaded as shown so as to removably receive an inlet coupling 22 or the inlet pipe 30 directly.

The inner apertures 124 are evenly spaced around the inner chamber and the through bores 122 are identically sized and evenly arrayed in a spoke-like fashion to ensure even pressure distribution of the fluid. This enables even filling of the multiple receptacles 26. There are eight connected receptacles 26, though more may be accommodated in the same manner. The solid body 120 of the distribution manifold 24 is desirably cylindrical with the through bores 122 being radially oriented. However, the shape may be other than cylindrical as long as the through bores 122 are evenly distributed to create an even filling pressure. For instance, the solid body 120 may be spherical, hemispherical, square, hexagonal or otherwise a regular polygon, etc.

In the same manner, the vent manifold 50 will be inverted relative to the fluid distribution manifold 24 in FIG. 6A, so that the larger inner cylindrical wall opens upward and forms the outlet 56. The closed upper surface of the fluid distribution manifold 24 is desirably flat, as is the closed lower surface of the vent manifold 50 such that the two manifolds can be positioned in abutting relationship, as indicated in FIGS. 3A and 3B. The two manifolds 24, 50 may be secured together with fusion or adhesive bonding.

FIGS. 8A-8D are perspective, plan, and elevational views of a combined fluid distribution manifold 140 and vent manifold 142 having the capacity for filling and venting 10 different connected receptacles. The physical configuration of the two manifolds 140, 142 is much the same as was described above with respect to the vent manifold 50, wherein both are formed of molded polymer bodies having a squat cylindrical shape, a common inlet or outlet along the central axis and radial passages 144, 146 through the outer circumferential walls. It should be noted that although the fluid distribution manifold 140 is positioned below the vent manifold 142, the positions could easily be reversed with minimal adjustment to the connecting conduits. The same applies to all other embodiments disclosed herein.

A first inner chamber 150 is formed by an inner cylindrical wall centrally located through an upper surface of the vent manifold 140. The radial passages 144 extend inward and open into a second inner chamber 152 also formed by an internal cylindrical wall. The first inner chamber 150 is larger than the second inner chamber 152 and defines a receptacle or port within which an outlet connector such as shown in 56 in FIG. 1 can be affixed. Although not shown, the same configuration of stepped inner chambers is provided at the bottom of the fluid distribution manifold 142.

If both the vent manifold 140 and fluid distribution manifold 142 are used, they may be separately molded or machined and then connected together through bonding, such as adhesive. There are 10 radial passages 144, 146 in each of the manifolds 140, 142, respectively, angularly spaced apart by an angle θ of 36°. As seen in FIGS. 8A-8D, the radial passages 144 are angularly offset by half that amount, or 18°, with respect to the radial passages 146. This helps provide space for the fluid and vent conduits that are connected around the conjoined manifolds 140, 142.

FIGS. 8B-8D illustrate a number of key dimensional parameters for the manifold 140, 142. In this embodiment, the two manifolds 140, 142 are identical and thus the dimensions that apply to one also apply to the other.

Each manifold 140, 142 defines an exterior diameter D, an inner diameter $d_i$ for the inner chamber, and an outer diameter $d_O$ for the outer chamber. The total exterior height H of the combined manifolds 140, 142 is shown, which may be twice the height of each of the manifolds separately. The height h from the adjacent lower or upper face of the respective manifold at which each of the radial passages 144, 146 are positioned is desirably one half of the height of that particular manifold. Each radial passage 144, 146 is angularly spaced an angle θ from the adjacent passage. An inner luminal diameter A of each radial passage 144, 146 is shown, as well as a diameter B of an outlet port. Exemplary values for each of these dimensional parameters is provided below in a table for the three manifolds shown. Dimensions for manifolds configured with a different number of radial passages or intended for use with particular fluids may be modified but fall within the general pattern disclosed.

FIGS. 9A-9C illustrate a still further stacked vent manifold 160 and fluid distribution manifold 162 having the capacity for filling and venting fourteen different connected receptacles, and FIG. 10 is a sectional view taken along the angled line 10-10 in FIG. 9B. As before, the two manifolds 160, 162 are both desirably formed of molded polymer bodies having a squat cylindrical shape, with a common inlet or outlet along the central axis and radial passages 164, 166 through the outer circumferential walls.

A first inner chamber 170 is formed by an inner cylindrical wall centrally located through an upper surface of the vent manifold 160. The radial passages 164 extend inward and open into a second inner chamber 172 also formed by an internal cylindrical wall. The first inner chamber 170 is larger than the second inner chamber 172 and defines a receptacle or port within which an outlet connector such as shown in 56 in FIG. 1 can be affixed. FIG. 10 is a cross-section which illustrates the same stepped inner chambers 174, 176 formed in the lower face of the fluid distribution manifold 162. Once again, the first inner chamber 174 provides a receptacle or port within which a common conduit such as the inlet pipe 30 shown above may be fastened. The smaller second inner chamber 176 opens outward to the radial passages 166.

If both the vent manifold 160 and fluid distribution manifold 162 are used, they may be separately molded or machined and then connected together through bonding, such as adhesive. There are 14 radial passages 164, 166 in each of the manifold 160, 162, respectively, angularly spaced apart an even amount, in this case about an angle θ of 25.7°. As seen in FIG. 9C, the radial passages 164 are angularly offset by half that amount with respect to the radial passages 166. This helps provide space for the fluid and vent conduits that are connected around the conjoined manifolds 160, 162.

The manifolds may have four or more inlets/outlets up to a practical maximum of 32. Of course, the size of the manifolds may have to be altered for greater number of connections. An even number makes fabrication easier, though the concept is not so limited.

TABLE I

Exemplary Dimensions for Disk-Shaped Fluid Distribution Manifolds (in.)

| | No. of Radial Outlets | | |
|---|---|---|---|
| | 8 | 10 | 14 |
| Overall dia. D | 1.000 | 1.500 | 2.500 |
| Inner dia. $D_i$ | 0.394 | 0.394 | 0.800 |
| Outer diameter $D_O$ | 0.518 | 0.518 | 1.000 |
| Overall Height H | 0.750 | 0.800 | 1.000 |
| Height h | 0.188 | 0.188 | 0.250 |
| Orifice dia. A | 0.094 | 0.125 | 0.110 |
| Port dia. B | 0.140 | 0.250 | 0.300 |

For each of the above exemplary dimension, tolerances of ±0.005 apply.

Terms such as top, bottom, left and right are used herein, though the fluid manifolds may be used in various positions such as upside down. Thus, some descriptive terms are used in relative terms and not absolute terms.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments.

As used herein, "plurality" means two or more. As used herein, a "set" of items may include one or more of such items. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It is claimed:

1. A system for distributing fluid from a single fluid source into multiple receptacles, comprising:
   a fluid distribution manifold comprising a solid body having a fluid inlet in communication with the single fluid source at a central location leading to an inner chamber, the fluid distribution manifold having a plurality of evenly spaced internal passages extending outward from a plurality of inner apertures opening to the inner chamber to a plurality of fluid outlets distributed evenly around an outer periphery of the body;
   a plurality of outlet conduits fluidly connected to the plurality of fluid outlets;
   a plurality of receptacles each of which has an outlet conduit connected thereto, wherein fluid provided to the fluid inlet of the fluid distribution manifold is distributed evenly through the internal passages, fluid outlets, and outlet conduits into the receptacles; and
   a gas vent disposed in each receptacle.

2. The system of claim 1, further comprising:
   a vent manifold disposed adjacent the fluid distribution manifold, the vent manifold having a solid body with a vent outlet at a central location leading to an inner chamber, the vent manifold having a plurality of evenly spaced internal passages extending outward from the inner chamber to multiple vent inlets distributed evenly around an outer periphery of the body;
   a plurality of vent conduits each of which connects one of the vent inlets of the vent manifold to one of the receptacle gas vents.

3. The system of claim 2, further comprising a common vent filter positioned to filter any gas which reaches the vent outlet of the vent manifold.

4. The system of claim 3, wherein the common vent filter is connected to an outlet tube sealed to the vent outlet of the vent manifold.

5. The system of claim 1, wherein the body has a cylindrical shape with the fluid inlet being circular and having an inlet pipe secured thereto and adapted to connect to the single fluid source.

6. The system of claim 1, wherein the body has a cylindrical shape with the fluid inlet being circular, and wherein the internal passages and fluid outlets extend radially outward from the inner chamber, the outlet conduits initially projecting radially outward from the body and bending 90° downward, and further including a common stand that maintains each of the receptacles in a vertical orientation below the fluid distribution manifold.

7. The system of claim 6, further comprising:
a vent manifold disposed above the fluid distribution manifold in an abutting relationship, the vent manifold having a cylindrical solid body with a vent outlet at a central location leading to an inner chamber, the vent manifold having a plurality of evenly spaced internal passages extending outward from the inner chamber to multiple vent inlets distributed evenly around an outer periphery of the body;
a plurality of vent conduits each of which connects one of the vent inlets of the vent manifold to one of the receptacle gas vents, the vent conduits initially projecting radially outward from the vent manifold body and bending 90° downward toward a respective receptacle gas vent.

8. The system of claim 1, wherein there are at least eight fluid outlets, outlet conduits, and receptacles.

9. The system of claim 8, wherein not all of the receptacles are the same size.

10. The system of claim 8, further including a flow control valve positioned along at least some of the outlet conduits.

11. A system for distributing fluid from a single fluid source into multiple receptacles, comprising:
a fluid distribution manifold comprising a solid body having a fluid inlet in communication with the single fluid source at a central location leading to an inner chamber, the fluid distribution manifold having a plurality of evenly spaced internal passages extending outward from a plurality of inner apertures opening to the inner chamber to a plurality of fluid outlets distributed evenly around an outer periphery of the body;
a plurality of outlet conduits fluidly connected to the plurality of fluid outlets;
a plurality of receptacles each of which has an outlet conduit connected thereto, wherein fluid provided to the fluid inlet of the fluid distribution manifold is distributed evenly through the internal passages, fluid outlets, and outlet conduits into the receptacles;
a gas vent disposed in each receptacle;
a vent manifold disposed adjacent the fluid distribution manifold in an abutting relationship, the vent manifold having a solid body with a vent outlet at a central location leading to an inner chamber, the vent manifold having a plurality of evenly spaced internal passages extending outward from the inner chamber to multiple vent inlets distributed evenly around an outer periphery of the body; and
a plurality of vent conduits each of which connects one of the vent inlets of the vent manifold to one of the receptacle gas vents, the vent conduits initially projecting radially outward from the vent manifold body and bending 90° downward toward a respective receptacle gas vent.

12. The system of claim 11, further comprising a common vent filter positioned to filter any gas which reaches the vent outlet of the vent manifold.

13. The system of claim 12, wherein the common vent filter is connected to an outlet tube sealed to the vent outlet of the vent manifold.

14. The system of claim 13, wherein there are at least two of the common vent filters connected in series.

15. The system of claim 11, wherein the fluid distribution manifold body has a cylindrical shape with the internal passages and fluid outlets extending radially outward from the inner chamber and the fluid inlet being circular and having an inlet pipe secured thereto and adapted to connect to the single fluid source, and the vent manifold body has a cylindrical shape with the internal passages extending and vent inlets extending radially outward from the inner chamber and the vent outlet being circular and having an outlet tube secured thereto.

16. The system of claim 15, wherein the outlet conduits and vent conduits initially project radially outward from the body and bend 90° downward, and further including a common stand that maintains each of the receptacles in a vertical orientation below the fluid distribution manifold and vent manifold.

17. The system of claim 16, wherein the outlet conduits and vent conduits are molded to the respective fluid outlets and vent inlets.

18. The system of claim 11, wherein there are at least eight fluid outlets, outlet conduits, and receptacles, and the same number of vent inlets and vent conduits.

19. The system of claim 11, wherein not all of the receptacles are the same size.

20. The system of claim 11, further including a flow control valve positioned along at least some of the outlet conduits.

* * * * *